United States Patent
Sati

(10) Patent No.: US 10,839,299 B2
(45) Date of Patent: Nov. 17, 2020

(54) NON-LEADING COMPUTER AIDED DETECTION OF FEATURES OF INTEREST IN IMAGERY

(71) Applicant: International Business Machines Corporation, Armonk, NY (US)

(72) Inventor: Marwan Sati, Ontario (CA)

(73) Assignee: International Business Machines Corporation, Armonk, NY (US)

(*) Notice: Subject to any disclaimer, the term of this patent is extended or adjusted under 35 U.S.C. 154(b) by 735 days.

(21) Appl. No.: 15/337,124

(22) Filed: Oct. 28, 2016

(65) Prior Publication Data

US 2018/0121813 A1 May 3, 2018

(51) Int. Cl.

| | |
|---|---|
| *G06N 5/04* | (2006.01) |
| *G06F 3/0484* | (2013.01) |
| *G06N 20/00* | (2019.01) |
| *G16H 30/40* | (2018.01) |
| *G16H 40/63* | (2018.01) |
| *G16H 30/20* | (2018.01) |
| *G06F 3/01* | (2006.01) |

(52) U.S. Cl.
CPC .............. *G06N 5/04* (2013.01); *G06F 3/017* (2013.01); *G06F 3/04842* (2013.01); *G06N 20/00* (2019.01); *G16H 30/20* (2018.01); *G16H 30/40* (2018.01); *G16H 40/63* (2018.01)

(58) Field of Classification Search
CPC .......... G06N 5/04; G06N 20/00; G06F 3/017; G06F 3/04842
See application file for complete search history.

(56) References Cited

U.S. PATENT DOCUMENTS

| | | | |
|---|---|---|---|
| 7,783,094 B2 * | 8/2010 | Collins | A61B 6/00 |
| | | | 382/128 |
| 8,498,492 B2 | 7/2013 | Declerck et al. | |
| 8,799,013 B2 | 8/2014 | Gustafson | |
| 2011/0210984 A1 * | 9/2011 | Wojton | A61B 5/444 |
| | | | 345/634 |
| 2015/0294445 A1 * | 10/2015 | Sakaue | G06T 7/33 |
| | | | 382/131 |
| 2016/0148371 A1 * | 5/2016 | Itu | A61B 8/06 |
| | | | 382/128 |
| 2016/0300349 A1 * | 10/2016 | Fonte | G06T 7/0012 |
| 2016/0342753 A1 * | 11/2016 | Feazell | G06N 7/005 |

* cited by examiner

*Primary Examiner* — Li B. Zhen
*Assistant Examiner* — Henry Nguyen
(74) *Attorney, Agent, or Firm* — Will Stock; Edell, Shapiro & Finnan, LLC

(57) ABSTRACT

An illustrative embodiment of a computer-implemented process for non-leading computer aided detection of features of interest in a dataset, designates a particular formation using a computer recognizable gesture to identify a gestured location in an analyzed view of the dataset in response to a user identifying the particular formation in the analyzed view. The dataset is generated by a computer and representative of a portion of an object characterized by the dataset. Responsive to identifying the gestured location, the particular formation is displayed to the user, and a composition is revealed including additional structural imagery, functional imagery and findings resulting from machine learning and analysis. Responsive to revealing the composition to the user, the user is prompted to select performance of accept selection, reject selection or modify selection with regard to the particular formation displayed.

23 Claims, 5 Drawing Sheets

NON-LEADING COMPUTER AIDED DETECTION OF FEATURES OF INTEREST IN IMAGERY

BACKGROUND

1. Technical Field

Present invention embodiments relate generally to the field of computer-aided detection (CAD) and analysis of physical structures using a data processing system and more specifically to automatic analysis of and detection of characteristics of physical structures represented within digital images using the data processing system.

2. Description of the Related Art

In the domain of the medical arts, Digital Imaging and Communications in Medicine (DICOM) is an industry standard created for the handling, storage, presentation, and transmission of information comprising medical imaging. DICOM is also known as NEMA standard PS3, and as ISO standard 12052:2006 *Health informatics—Digital imaging and communication in medicine*. The standard includes information for workflow and data management of medical imaging information.

The specification and further information may be obtained from a standards website found at dicom.nema.org/ The standard includes a definition for a particular file format as well as a network communications protocol used to transmit the information. The communication protocol chosen is a particular application that uses TCP/IP to handle the communication between source and target systems. An implementation using the DICOM files can therefore exchange the files between two systems that support the standard and are therefore capable of receiving the medical images and patient data using the specified DICOM format.

The current systems typically compute an initial diagnosis based on a set of identified features and a diagnosis model, which are provided to a user for review and modification. A computed diagnosis is dynamically re-computed upon modification of the set of identified features by the user. Upon the user selecting a diagnosis based on a system recommendation, a diagnosis report is generated reflecting the features present in the digital image as validated by the user and the user selected diagnosis.

One of the issues facing users of digital imaging in medicine is that the computer technology may pose too great an influence in a decision of a doctor. This influence or bias may cause users to look into areas that they would not normally suspect leading to "false positives" and excessive treatment of patients. Furthermore, with traditional CAD methods there is a risk that the user becomes overly dependent on the CAD findings and does not look through the entire image. This can lead to missed findings when the CAD algorithm fails to correctly determine a possible area.

SUMMARY

According to an embodiment of the present invention, a computer-implemented process for non-leading computer aided detection of features of interest in a dataset, designates a particular formation using a computer recognizable gesture to identify a gestured location in an analyzed view of the dataset in response to a user identifying the particular formation in the analyzed view of the dataset generated by the computer using machine learning and analysis and representative of a portion of an object characterized by the dataset. In response to identifying the gestured location, the computer displays the particular formation to the user, revealing a composition including additional structural imagery, functional imagery and findings resulting from the machine learning and analysis. The user is prompted by the computer to perform one of accept selection, reject selection or modify selection with regard to the composition revealed in response to revealing the composition to the user, including the additional structural imagery, functional imagery and findings from the machine learning and analysis associated with the particular formation displayed.

BRIEF DESCRIPTION OF THE DRAWINGS

For a more complete understanding of this disclosure, reference is now made to the following brief description, taken in conjunction with the accompanying drawings and detailed description, wherein like reference numerals represent like parts.

DETAILED DESCRIPTION

Figure 1:
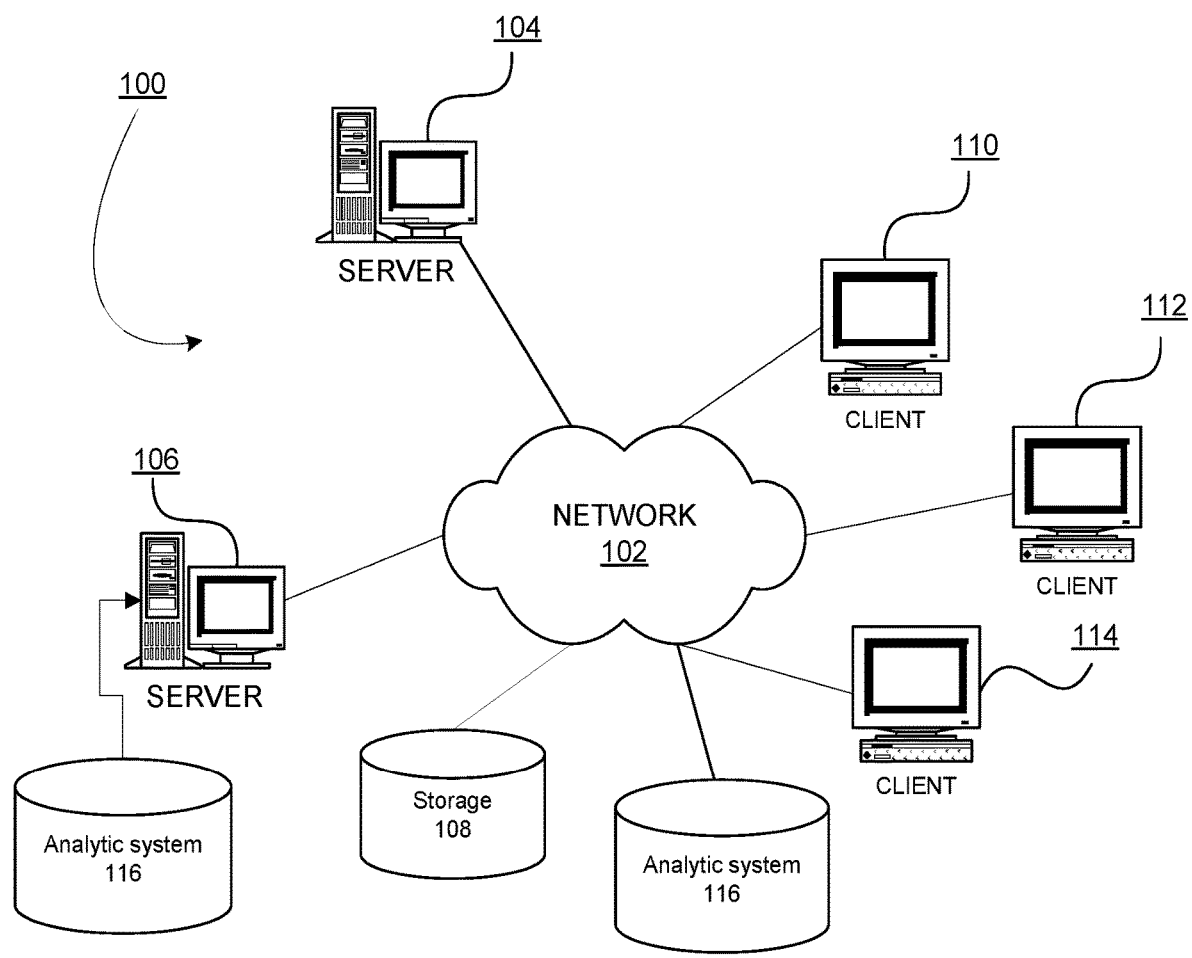
FIG. 1 is a block diagram of an example network data processing system operable for various embodiments of the disclosure.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
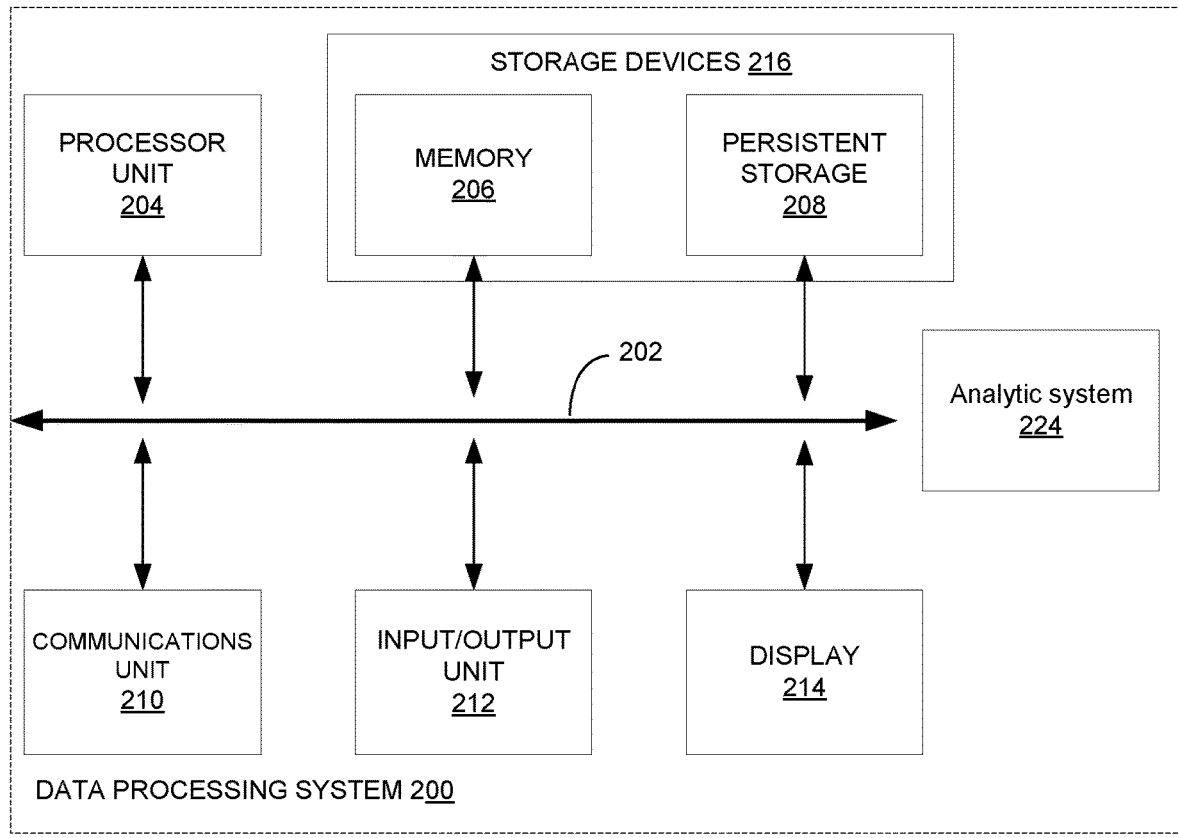
FIG. 2 is a block diagram of an example data processing system operable for various embodiments of the disclosure.
Figure 2:
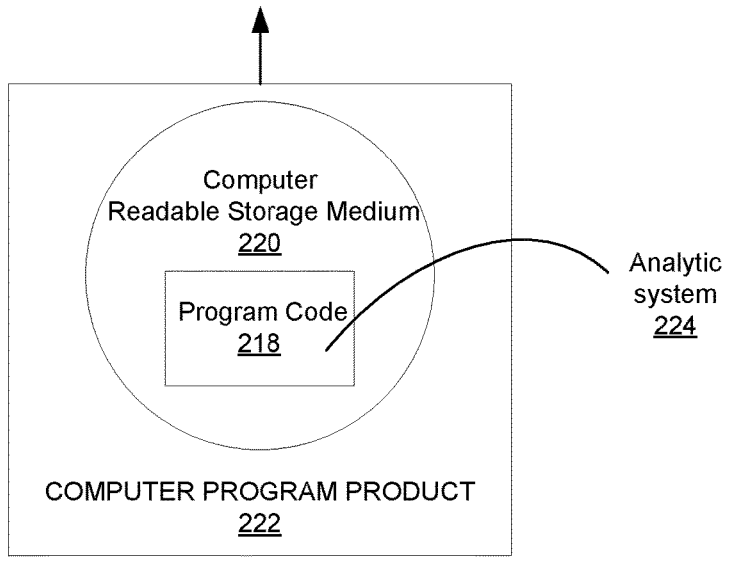

With reference now to the figures and in particular with reference to FIGS. 1-2, example diagrams of data processing environments are provided in which illustrative embodiments may be implemented. It should be appreciated that FIGS. 1-2 are only examples and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, analytic system 116 and applications to clients 110, 112, and 114. Clients 110, 112, and 114 are clients to server 104 in this example. In addition analytic system 116 may also be directly connected to network 102. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP)

suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference to FIG. 2 a block diagram of an example data processing system operable for various embodiments of the disclosure is presented. In this illustrative example, data processing system 200 includes communications fabric 202, which provides communications between processor unit 204, memory 206, persistent storage 208, communications unit 210, input/output (I/O) unit 212, display 214 and analytic system 224.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices 216. A storage device is any piece of hardware that is capable of storing information, such as, for example without limitation, data, program code in functional form, and/or other suitable information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208. In another example, analytic system 224 may also be contained within memory 206 or persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard, a mouse, and/or some other suitable input device. Further, input/output unit 212 may send output to a printer. Display 214 provides a mechanism to display information to a user.

Instructions for the operating system, applications and/or programs may be located in storage devices 216, which are in communication with processor unit 204 through communications fabric 202. In these illustrative examples the instructions are in a functional form on persistent storage 208. These instructions may be loaded into memory 206 for execution by processor unit 204. The processes of the different embodiments may be performed by processor unit 204 using computer-implemented instructions, which may be located in a memory, such as memory 206.

These instructions are referred to as program code, computer usable program code, or computer readable program code that may be read and executed by a processor in processor unit 204. The program code in the different embodiments may be embodied on different physical or tangible computer readable storage media, such as memory 206 or persistent storage 208.

Program code 218 is located in a functional form on computer readable storage media 220 that is selectively removable and may be loaded onto or transferred to data processing system 200 for execution by processor unit 204. Program code 218 and computer readable storage media 220 form computer program product 222 in these examples. In one example, computer readable storage media 220 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable storage media 220 also may take the form of a persistent storage, such as a hard drive, a thumb drive, or a flash memory that is connected to data processing system 200. The tangible form of computer readable storage media 220 is also referred to as computer recordable storage media or a computer readable data storage device. In some instances, computer readable storage media 220 may not be removable. In one example, program code 218 contains program code which when executed causes analytic system 224 to be fully functional.

Alternatively, program code 218 may be transferred to data processing system 200 from computer readable storage media 220 through a communications link to communications unit 210 and/or through a connection to input/output unit 212. The communications link and/or the connection may be physical or wireless in the illustrative examples.

In some illustrative embodiments, program code 218 may be downloaded over a network to persistent storage 208 from another device or data processing system for use within data processing system 200. For instance, program code stored in a computer readable data storage device in a server data processing system may be downloaded over a network from the server to data processing system 200. The data processing system providing program code 218 may be a server computer, a client computer, or some other device capable of storing and transmitting program code 218.

Using data processing system 200 of FIG. 2 as an example, a computer-implemented process for non-leading computer aided detection of features of interest in a dataset is presented. Processor unit 204, in response to a user identifying a particular structure in an analyzed view of the dataset generated by processor unit 204 and representative of a portion of an object characterized by the dataset, designates the particular structure using a computer recognizable gesture to identify a gestured location in the analyzed view of the dataset. In response to identifying the gestured location, processor unit 204 displays the particular structure to the user, including additional structural imagery associated with the particular structure. In response to revealing the particular structure to the user, including additional structural imagery associated with the particular structure displayed, the user is prompted by processor unit 204 to perform one of accept selection, reject selection or modify selection with regard to the particular structure the computer displayed.

In another example using data processing system 200 of FIG. 2 a computer-implemented process for non-leading computer aided detection of features of interest in a dataset is presented. Processor unit 204, designates a particular formation using a computer recognizable gesture to identify a gestured location in an analyzed view of the dataset in response to a user identifying the particular formation in the analyzed view of the dataset generated by the computer using machine learning and analysis and representative of a portion of an object characterized by the dataset. Processor unit 204 displays the particular formation to the user, revealing a composition including additional structural imagery, functional imagery and findings resulting from the machine learning and analysis, in response to identifying the gestured location. Processor unit 204 further prompts the user to perform one of accept selection, reject selection or modify selection with regard to the composition revealed in response to revealing the composition to the user, including the additional structural imagery, functional imagery and findings from the machine learning and analysis associated with the particular formation displayed.

Figure 3:
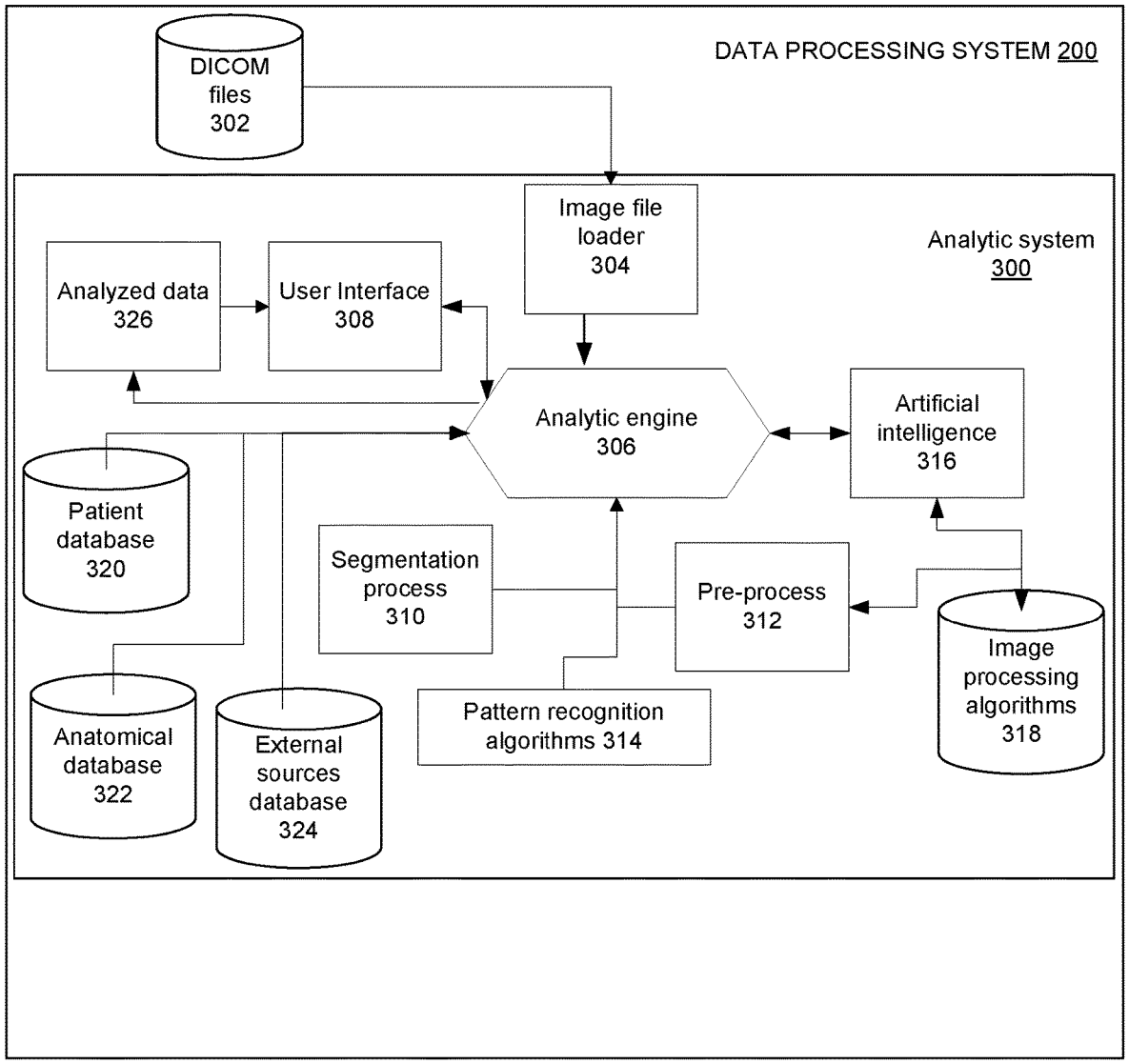
FIG. 3 is a block diagram representation of an analytic system operable for various embodiments of the disclosure.

With reference to FIG. 3 a block diagram of an analytic system operable for various embodiments of the disclosure is presented. Analytic system 300 is an example of an embodiment of the disclosure.

Analytic system 300 comprises a number of components including DICOM files 302, image file loader 304, analytic engine 306, user interface 308, segmentation process 310, pre-process 312, pattern recognition algorithms 314, artificial intelligence 316, image processing algorithms 318, patient database 320, anatomical database 322, external sources database 324 and analyzed data 326. These components may be implemented as described or in some functional combination or combinations as required for a particular implementation without loss of function.

DICOM files 302 are particular formatted image data files that conform to the industry standard for Digital Imaging and Communications in Medicine. These specifically formatted data files are used to provide scanned image information from various medical imaging devices as input to analytic system 300. Image file loader 304 is a particular software component providing a capability to receive DICOM files 302 and make the files available for processing by analytic engine 306.

Analytic engine 306 provides a set of program code, which when executed uses combinations of other specified components to process one or more DICOM files 302 into analyzed data 326. Results of processing DICOM files 302 including analyzed data 326 are presented using user interface 308. A user may control the processing of analytic system 300 through user interface 308.

Analytic engine 306 selectively uses artificial intelligence 316 in combination with image processing algorithms 318 to process DICOM files 302 to create analyzed data 326. For example, image-processing algorithms 318 includes specialized routines comprising routines to handle specific anatomical objects as well as pathological information. Artificial intelligence 316 includes specialized code to "learn" through prior processing and therefore add to the capability of analytic engine 306. A "Watson intelligent machine" (available from International Business Machines Corporation) is one example of an intelligent analytic engine used to analyze one or more digital images to identify anatomical structures comprising organs, lesions and other "objects of interest."

Segmentation process 310 provides a capability to analytic engine 306 to identify portions of the digital images contained within DICOM files 302 including organs, tissue and other objects such as skeletal elements of patients. Pre-process 312 provides a capability to analytic engine 306 to identify portions of the digital images contained within DICOM files 302 that require modification prior to subsequent processing. For example, one or more received DICOM files 302 may comprise an unacceptable level of noise or the image may be improperly exposed. Pre-process 312 is used to resolve these types of problems with the images provided as input and therefore improve subsequent processing of DICOM files 302.

Pattern recognition algorithms 314 provides a capability to analytic engine 306 to compare structural elements identified by analytic engine 306 with previously identified structures maintained in patient database 320, anatomical database 322 and external sources database 324. Patient database 320 contains information comprising individual patient information and aggregate patient information and associated pathological information for identifying anomalies within particular anatomical structures including bones and organs within a patient. For example, for a particular patient, patient database 320 contains information from previous scans, assessments and diagnosis, which are used along with subsequent scans, assessments and diagnosis. Anatomical database 322 contains information with regard to health information specifically for anatomical structures of people and associated pathological information for identifying anomalies within particular anatomical structures including bones and organs within a patient.

External sources database 324 contains information comprising anatomical and pathological information for identifying anomalies within particular anatomical structures including bones and organs within a patient. This information enhances the capability of the analytic engine 306 and analytic system 300 through additional information from additional information sources. There are a number of other potential patient-specific inputs for one or more selected algorithms to analyze the images including: information from electronic medical records, for example, a chief complaint, a medical history, including any previous findings for that patient, and a Medical Order (usually through Heath Level 7, international standards for transfer of information broadly described as either clinical or administrative in nature and available from www.hl7.org). The selected algorithm will focus the analysis for which the imaging study was ordered to use the information from the Medical Order. For example if the exam was ordered to follow up on liver cancer the algorithm would include that information in its search for tumors within an image of the liver. Moreover, prior medical images 302 can be registered through image processing 318 with the current medical image to help the algorithms determine where to look for disease progression in the current medical image.

An embodiment of analytic system 300 provides a capability to the user to select suspected areas and prompt analytic system 300 to reveal whatever characteristics of the specified area that the system has determined. The suspected area selected by the user is typically influenced by information including visual cues, clinical indications of the chief medical complaint, completing information from prior diagnoses, and common locations of disease. Regulatory bodies would typically be more comfortable with this approach because the medical professional remains in control of the process and diagnosis, is less biased and therefore less likely to miss any finding due only to gaps in machine learning.

Figure 4:
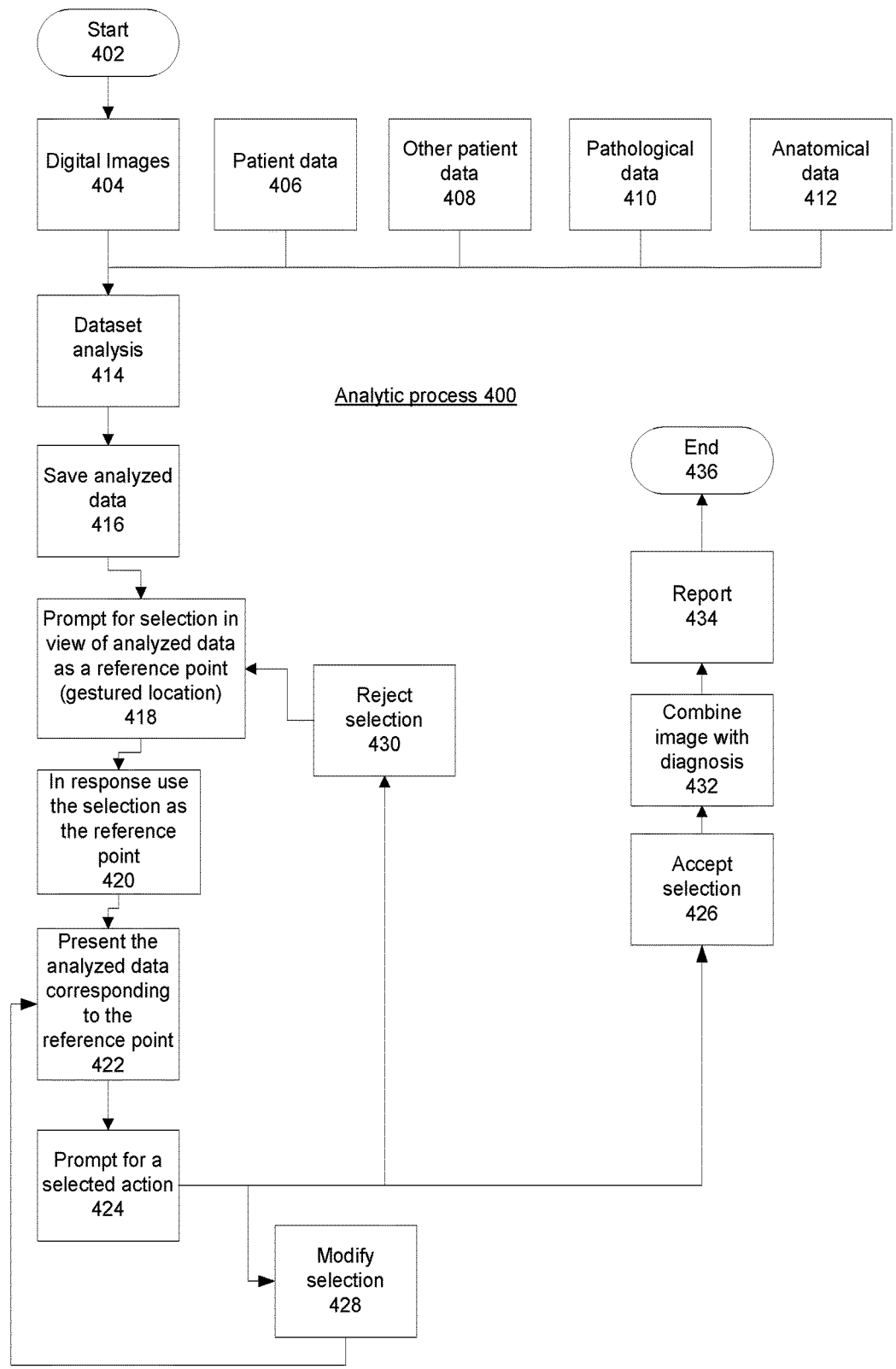
FIG. 4 is a flowchart of an analytic process using analytic system 300 of FIG. 3 in accordance with one embodiment of the disclosure.

With reference to FIG. 4 an analytic process operable for various embodiments of the disclosure is presented. Analytic process 400 is an example of a computer-implemented process using analytic system 300 of FIG. 3.

Continuing with the example of analytic system 300 of FIG. 3, analytic process 400 is an example process in which a dataset is analyzed to reveal functional as well as structural details and other findings as a result of machine learning and analysis within the dataset. In the current example, analytic process 400 starts, (step 402) when input data is received for processing. The dataset provided as input to analytic process 400 is a set of one or more digital images 404, typically DICOM images in the example, but the process is not restricted to only this type of input or a process specific to image data. Additionally the input contains information associated with digital images 404 including patient data 406, other patient data 408, pathological data 410 and anatomical data 412. Furthermore, the input may be augmented by information from external sources such as that found in external sources database 324 of FIG. 3 including but not limited to prior patient data, and exam order information. Other patient data 408 is associated with other patients viewed as cohorts due to similarity in actual or suspected health context.

Analytic process 400 performs a structural analysis, a functional analysis or a combination thereof (step 414). For example, the analysis performed is a functional analysis when analyzing information associated with the metabolism of a tumor. Whenever a predetermined amount of analysis is completed or at predetermined checkpoints, saving of analyzed data (step 416) is performed. The saving of analyzed data at known points in the process is also made known to a user of the process. The user is therefore aware of progress in the process as well as when the process may be complete for a particular analysis. For example, when a predetermined algorithm used by the computer in analytic process 400 is not yet finished performing an analysis, the computer will reveal only what has been identified up to a current point of processing, indicating that the algorithm is not yet done. In this example, analytic process 400 provides an indication of a current status of completion of the analysis at the current point. In addition an estimated time of completion from the current point may be provided by analytic process 400. The user is further notified when analytic process 400 is finished.

Analytic process 400 prompts for a selection in view of the analyzed data as a reference point (step 418). The user using a gesture to the system indicates the reference point. The gesture may be the result of an action including one of a mouse click, eye tracking, and touch screen. The gesture location indicates an area or point of interest for which the user requests the system findings particular to that area by way of the gestured location. The reference point is also referred to as a gestured location. The gestured location refers to a composition including additional structural imagery, functional imagery and findings from the machine learning and analysis associated with a particular formation displayed.

In one embodiment, steps 402-416 of analytic process 400 may be pre-processed before the user provides a gestured input to indicate that information for the particular area is to be revealed. In another embodiment, steps 402-416 of analytic process 400 may alternatively be processed in real time when the processing system has sufficient capacity and is responsive enough. However, when pre-processing is performed mid-stream due to the user requesting analysis, analytic process 400 will reveal what it has found to up to that point in processing. Furthermore, analytic process 400 will notify the user that further analysis is underway so that the user has an option to allow the system more time to complete processing.

Analytic process 400 in response to a selection uses the selection as the reference point (step 420). Data corresponding to the reference point is presented (to the user) by analytic process 400 (step 422). The data is revealed as the composition to the user, including the additional structural imagery, functional imagery and findings from the machine learning and analysis associated with the particular formation displayed. In response to presenting the data corresponding to the reference point, analytic process 400 prompts for a selected action (step 424). The prompt is directed toward the user with respect to the data presented to identify a particular action to be performed. The selection of actions is made from a set or group of actions comprising accept selection (step 426), modify selection (step 428) and reject selection (step 430).

Responsive to receiving accept selection (step 426), in response to the prompt for a selected action, analytic process 400 combines the image with a diagnosis (step 432) and generates a report (step 434) terminating thereafter (step 436). Responsive to receiving modify selection (step 428), in response to the prompt for a selected action, analytic process 400 loops back to perform step 422 as before. The user is then permitted to perform changes as necessary. Upon completion of the modifications, analytic process 400 then performs step 424 as before. Responsive to receiving reject selection (step 430), in response to the prompt for a selected action, analytic process 400 loops back to perform step 418 as before.

In the field of radiology, CAD may also be referred to as computer-aided diagnosis. Such procedures used in the medicinal arts provide assistance to doctors when interpreting medical images. Imaging techniques including use of X-ray, magnetic resonance imaging (MRI), and ultrasound diagnostics are used to provide a great deal of useful information, which a radiologist must then analyze and evaluate in a typically short time. The CAD systems provide assistance in the scan of digital images, for example from a computed tomography, which uses computer-processed combinations of multiple X-ray images taken from a set of differing angles or views to produce generated cross-sectional (tomographic) images which represent a number of virtual slices or views of specific portions of a scanned object. The virtual views are analyzed for typical appearances usually referred to as "unremarkable" and also to highlight sections, which may contain anomalies representative of diseases.

The CAD process therefore combines elements of artificial intelligence, computer presentation with image processing technology in the field of radiology. Typical usage of CAD is found in the search for and detection of tumors in patients. CAD systems are enhanced to provide diagnosis systems that further evaluate any conspicuous structures detected using algorithms designed for pattern recognition in anatomical tissue.

In a typical process a server executing a CAD application receives the digital image data obtained from a set of scans for a patient. The digital image data is in a DICOM-format and processed in a series of operations. Preprocessing may be used to prepare the digital image data by elimination of unwanted elements, reduction of "noise" and improving image quality, for example, by correcting under or over exposure. Segmentation may also be used to identify and differentiate the various structures contained within the digital image, including organs, bones, and growths. Matching of the identified structures with known structures of an anatomic repository may also occur to further identify objects within the digital image.

Any structure identified is analyzed according to a predetermined set of criteria including shape, size, location, proximity to other objects and gradient (typical grey scale image in which a degree of light or dark grey may indicate intake of a contrast agent used to help isolate tumors.

After structural analysis, the identified objects are evaluated according to a predetermined threshold level. Objects that exceed predetermined threshold level are highlighted in the digital image for viewing by the radiologist. However, the CAD systems are typically set to highlight one or more types of suspicious structures. Because the CAD systems cannot detect all anatomical changes due to disease an incorrect selection of healthy anatomical segments results in a false positive finding. A low specificity resulting from false positive findings reduces confidence in the CAD system because the radiologist then has to identify the wrong presentations from the correct presentations. CAD systems may also miss findings. For example, missed findings may be due to low sensitivity to data used in a particular CAD algorithm.

Therefore a CAD system, which leads the radiologist using incorrectly identified structures, may lead the radiologist toward an incorrect diagnosis. However, in an embodiment of the disclosed system, the system receives the digital image of a patient and using machine intelligence investigates findings by performing a set of operations including analyzing the image, seeking prior anatomical information for that patient, examining associated literature, and correlating anatomical information for similar patients. This set of operations typically requires a number of actions that can take a significant amount of time. For example, time to seek out the prior anatomical information for that patient, similar images, and associated literature and therefore cannot typically be accomplished "on the fly." In addition some elements of pre-processing can invoke other requests for information that also have time delays.

Analytic process 400 will only reveal the findings when prompted by the user using a gestured location. In this way the system is not distracting the radiologist with too much information and falsely influencing the radiologist to look into areas that they would not otherwise typically explore. Analytic process 400 enables the radiologist to continue view the digital image as a whole while quickly generating diagnostic information for a suspect area using the gestured location.

In a previous solution, which does not use analytic process 400, a radiologist typically selects a starting point for an analysis from a seed point in a digital image. This selection of a starting point is a very common approach that is a standard practice in the field currently. A display of detected features is then calculated using the seed point, also referred to as region of interest. A modification of the features can then be used for a diagnosis and a medical report. Therefore, the prior solutions only start after a user has selected a suspicious object in the digital image. In contrast with prior solutions, an embodiment of analytic process 400 analyzes an entire image and generates a set of determinations with regard to all regions of the image. The system only reveals what findings exist when a user indicates that the information in a specified area (the gestured location) is to be revealed.

For example, in one embodiment of analytic process 400 an analytic engine, described as analytic engine 306 of FIG. 3, may be in the form of a "Watson intelligent machine" (available from International Business Machines Corporation) to analyze one or more digital images to identify anatomical structures comprising organs, lesions and other "objects of interest." The analytic engine "knows" what to search for in the digital images using patient meta-data including patient history, DICOM header and other "context-based identification." For example, a particular algorithm is selected to automatically detect one of a number of cancer lesions in a liver as well as automatically detecting the liver in the digital image of the respective patient.

In contrast with previous CAD solutions, analytic process 400 in an embodiment of this disclosure does not "reveal" findings to a user, as typically done in prior solutions that use prompting for a selection of a set of diagnosis. Using an embodiment of analytic process 400, the user scans through the digital image, and in response to an area of interest coming into view; the user selects a particular structure (or portion thereof) in the view using a computer-recognized gesture. Only after a specific "gesture location" is indicated does the system "reveal" structural information, functional information or portion thereof (for example, a lesion) that was found within the view of the digital image. Using analytic process 400, the computer is therefore not suggesting where the lesion is located. Instead the computer is merely revealing only what anatomical structures or functional information was found at the gestured location. The user then proceeds to accept, reject or modify what the computer found at the selected location.

Embodiments of analytic process 400 may also be extended beyond the particular healthcare and imaging examples used herein. Embodiments of analytic process 400 potentially apply to any domain that provides feedback to a requesting user, without a potential for biasing views of the requesting user, as desired or required by regulatory policies. Embodiments of analytic process 400 use a particular dataset that is representative of information specific to data selected from a group consisting of Medical EKG/ECG/EEG data, Medical sleep study data, Medical pathology data, Geological data, Aerial/Satellite surveillance data and online research using locations within an online document.

For Medical EKG/ECG/EEG data the user would select a portion of the readings that show a suspicious pattern. The computer would reveal information that it found related to that abnormal condition such as previous studies with similar findings, family history of similar condition, cardiac image findings related to the condition and electrophysiology data corresponding to the condition. Those other pieces of information can help the medical professional come to a conclusion regarding the suspicious electrocardiogram or electroencephalogram data.

For medical sleep data the user would select a suspicious portion of the sleep study readings (including heart rate, wake cycles, EKG, oxygen saturation, and leg movement). The computer would reveal information related to that suspicious finding including history of sleep apnea, history of cardiac abnormalities, body mass index (BMI), medications, prior sleep studies of same patient with similar patterns.

For suspicious medical pathology data the system would reveal information including relevant lab results on genetic pre-disposition to the related disease, family history of the disease, prior pathology slides of the same patient with similar findings.

For Geological data the user would select an area of interest for example, in a seismic dataset. The system would reveal other associated information such as geological survey information in that area, other sub terrestrial images of that area, satellite images of the area, ground water models of the area.

For Aerial/Satellite surveillance information the user would select an area of interest including abnormal carbon monoxide (CO) levels in an area from satellite imagery. The system would provide data related to the finding including location of closest factories emitting CO, historical values in that area, wind patterns, and forest fire history.

Figure 5:
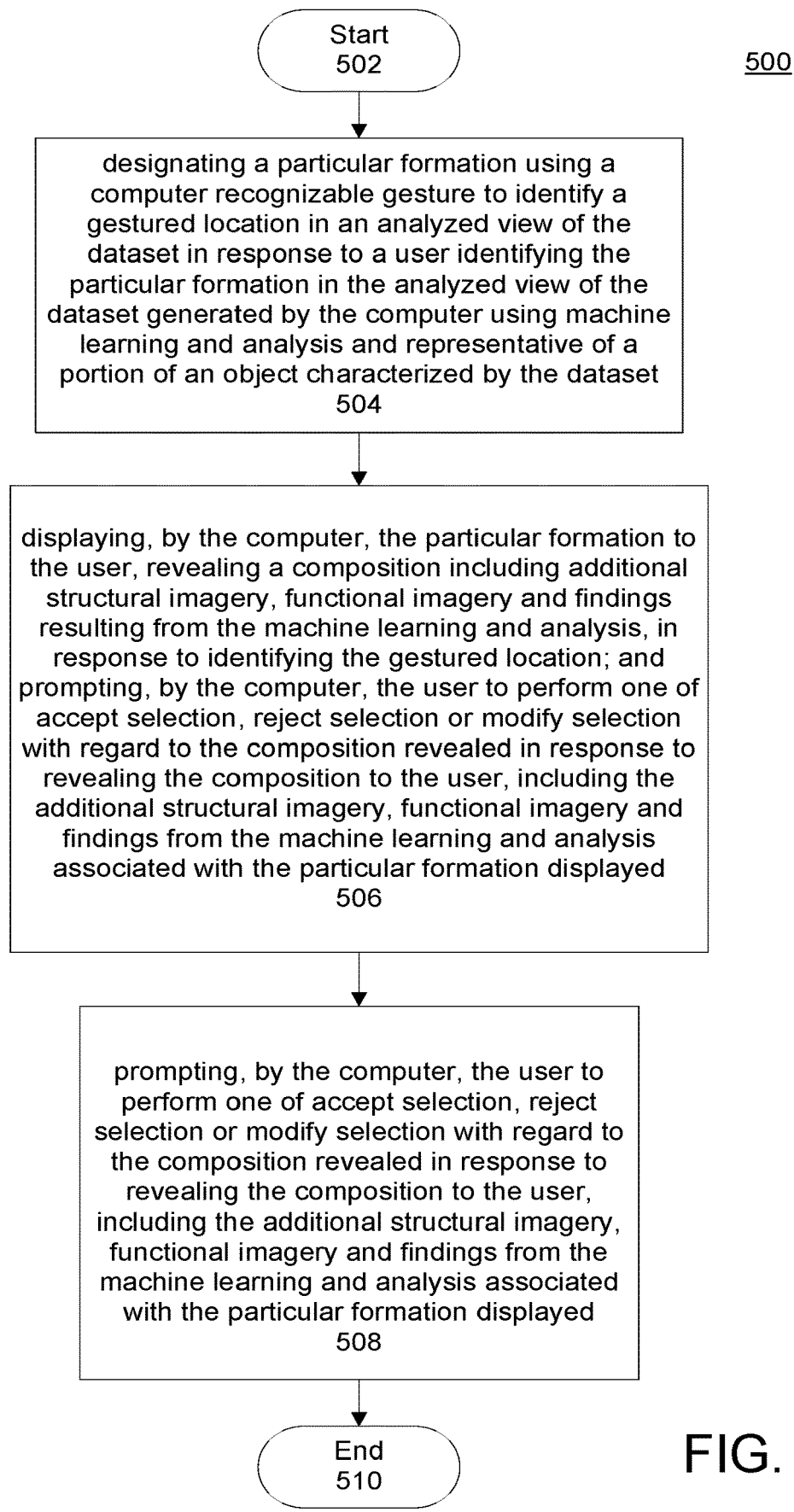
FIG. 5 is a flowchart of an analytic process using analytic system 300 of FIG. 3 in accordance with one embodiment of the disclosure.

With reference to FIG. 5 an analytic process operable for various embodiments of the disclosure is presented. Analytic process 500 is an example of a computer-implemented process using analytic system 300 of FIG. 3.

Analytic process 500 starts (step 502) and begins a process for non-leading computer aided detection of features of interest in a dataset. Analytic process 500 designates a particular formation using a computer recognizable gesture to identify a gestured location in an analyzed view of the dataset in response to a user identifying the particular formation in the analyzed view of the dataset generated by the computer using machine learning and analysis and representative of a portion of an object characterized by the dataset (step 504).

Analytic process 500 further displays, using the computer, the particular formation to the user, revealing a composition including additional structural imagery, functional imagery and findings resulting from the machine learning and analysis, in response to identifying the gestured location, and prompts, using the computer, the user to perform one of accept selection, reject selection or modify selection with regard to the composition revealed in response to revealing the composition to the user, including the additional structural imagery, functional imagery and findings from the machine learning and analysis associated with the particular formation displayed (step 506). Analytic process 500 further prompts, again using the computer, the user to perform one of accept selection, reject selection or modify selection with regard to the composition revealed in response to revealing the composition to the user, including the additional structural imagery, functional imagery and findings from the machine learning and analysis associated with the particular formation displayed (step 508) and terminates thereafter (step 510).

Thus is presented in an illustrative embodiment a computer-implemented process for non-leading computer aided detection of features of interest in a dataset. The computer-implemented method designates a particular formation using a computer recognizable gesture to identify a gestured location in an analyzed view of the dataset in response to a user identifying the particular formation in the analyzed view of the dataset generated by the computer using machine learning and analysis and representative of a portion of an object characterized by the dataset. The computer-implemented method further displays, by the computer, the particular formation to the user, revealing a composition including additional structural imagery, functional imagery and findings resulting from the machine learning and analysis, in response to identifying the gestured location. The computer-implemented method further prompts, by the computer, the user to perform one of accept selection, reject selection or modify selection with regard to the composition revealed in response to revealing the composition to the user, including the additional structural imagery, functional imagery and findings from the machine learning and analysis associated with the particular formation displayed.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing a specified logical function. It should also be noted that, in some alternative implementations, the functions noted in the block might occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, and other software media that may be recognized by one skilled in the art.

It is important to note that while the present invention has been described in the context of a fully functioning data processing system, those of ordinary skill in the art will appreciate that the processes of the present invention are capable of being distributed in the form of a computer readable data storage device having computer executable instructions stored thereon in a variety of forms. Examples of computer readable data storage devices include recordable-type media, such as a floppy disk, a hard disk drive, a RAM, CD-ROMs, DVD-ROMs. The computer executable instructions may take the form of coded formats that are decoded for actual use in a particular data processing system.

A data processing system suitable for storing and/or executing computer executable instructions comprising program code will include one or more processors coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

What is claimed is:

1. A computer-implemented process for non-leading computer aided detection of features of interest in a dataset, the computer-implemented process comprising:
    generating an analyzed view of the dataset by the computer by analyzing the dataset using machine learning and analysis of the dataset and associated data derived from one of an internal source and an external source and storing results of the machine learning and analysis after predetermined checkpoints each corresponding to performing a predetermined amount of the analyzing, wherein the analyzed view includes analysis for a plurality of formations within the dataset, and wherein the analyzing using machine learning and analysis produces for the plurality of formations within the dataset additional structural imagery, functional imagery and findings including prior anatomical information of a patient, associated literature, and anatomical information correlated from other patients with a corresponding medical condition;
    designating a particular formation using a computer recognizable gesture to identify a gestured location in the analyzed view of the dataset associated with the particular formation, wherein the particular formation of the analyzed view of the dataset is representative of a portion of an object characterized by the dataset;
    displaying, by the computer, the particular formation to a user, and revealing a composition for the particular formation including additional structural imagery, functional imagery and findings resulting from the machine learning and analysis of the plurality of formations of the dataset, in response to identifying the gestured location, wherein when the machine learning and analysis are prior to completion, the revealing further comprising:
        revealing the composition for the particular formation including the additional structural imagery, functional imagery and findings up to a current point of processing; and
        providing additional time for completion of the machine learning and analysis in response to an indication from the user; and
        prompting, by the computer, the user to select performance of one of accept selection, reject selection and modify selection with regard to the composition revealed in response to revealing the composition to the user, wherein the composition includes the additional structural imagery, functional imagery and findings from the machine learning and analysis associated with the particular formation displayed.

2. The computer-implemented process of claim 1, wherein the dataset is representative of information specific to data selected from a group consisting of Medical EKG/ECG data, Medical sleep study data, and Medical pathology data.

3. The computer-implemented process of claim 1, wherein in response to a predetermined algorithm used by the computer that has not finished performing the analysis, the computer revealing what has been identified up to a current point in processing, and indicating that the predetermined algorithm has not finished;
    providing an indication of a current status of completion of the analysis at the current point in processing;
    providing an estimated time of completion of the analysis from the current point in processing; and
    prompting the user when finished.

4. The computer-implemented process of claim 1, wherein the computer recognizable gesture is an action including a single "mouse click" to identify the gestured location in the analyzed view, and wherein the dataset includes a medical image that conforms to a DICOM format.

5. The computer-implemented process of claim 1, wherein performing accept selection further comprises:
    combining the particular formation, including the additional structural imagery, functional imagery and findings resulting from the machine learning and analysis associated with the particular formation displayed, with a diagnosis; and
    generating a report including the diagnosis.

6. The computer-implemented process of claim 1, wherein performing reject selection further comprises:
    prompting, by the computer, the user for selection of another gestured location in a view of the particular formation, including the additional structural imagery, functional imagery and findings resulting from the machine learning and analysis associated with the particular formation displayed.

7. The computer-implemented process of claim 1, wherein performing modify selection further comprises:
    presenting the particular formation corresponding to the gestured location after a modification, including the additional structural imagery, functional imagery and findings resulting from the machine learning and analysis associated with the particular formation displayed.

8. A computer-implemented process for non-leading computer aided detection of features of interest in medical imagery, the computer-implemented process comprising:
    receiving, by a computer, one or more digital images;
    receiving, by the computer, one or more of patient data, other patient data, pathological data and anatomical data, wherein the pathological data and the anatomical data are derived from one of an internal source and an external source to form a dataset including the one or more digital images received;
    performing, by the computer, an analysis of the dataset using machine learning and storing results of the machine learning and analysis after predetermined checkpoints each corresponding to performing a predetermined amount of the analysis,
    wherein the analyzed data includes analysis for a plurality of formations within the dataset, and wherein the analysis using machine learning produces for the plurality of formations within the dataset additional structural imagery, functional imagery and findings including prior anatomical information of a patient, associated literature, and anatomical information correlated from other patients with a corresponding medical condition;

prompting, by the computer, a user for a selection of a particular formation using a gestured location in a view of the analyzed data associated with the particular formation revealing a composition for the particular formation including additional structural imagery, functional imagery and findings resulting from the machine learning and analysis of the plurality of formations;

presenting, by the computer, the composition corresponding to the gestured location of the user associated with the particular formation, including the additional structural imagery, functional imagery and findings resulting from the machine learning and analysis of the plurality of formations, wherein when the machine learning and analysis are prior to completion, the presenting further comprising:

revealing the composition for the particular formation including the additional structural imagery, functional imagery and findings up to a current point of processing; and providing additional time for completion of the machine learning and analysis in response to an indication from the user;

prompting, by the computer, the user for a selected action from a set of actions consisting of accept selection, reject selection and modify selection;

in response to the selected action being the reject selection, further prompting the user for a selection of a new gestured location in a view of the composition for the particular formation including the additional structural imagery, functional imagery and findings resulting from the machine learning and analysis of the plurality of formations;

in response to the selected action being the modify selection, presenting the composition corresponding to the gestured location of the user associated with the particular formation after a modification, including the additional structural imagery, functional imagery and findings resulting from the machine learning and analysis of the plurality of formations;

in response to the selected action being the accept selection, combining the composition for the particular formation, including the additional structural imagery, functional imagery and findings resulting from the machine learning and analysis of the plurality of formations, with a diagnosis; and generating a report.

9. A computer program product for non-leading computer aided detection of features of interest in a dataset, the computer program product comprising:

one or more computer readable storage media collectively containing computer executable program code stored thereon for execution by a computer, the computer executable program code comprising:

computer executable program code for generating an analyzed view of the dataset by analyzing the dataset using machine learning and analysis of the dataset and associated data derived from one of an internal source and an external source and storing results of the machine learning and analysis after predetermined checkpoints each corresponding to performing a predetermined amount of the analyzing, wherein the analyzed view includes analysis for a plurality of formations within the dataset, and wherein the analyzing using machine learning and analysis produces for the plurality of formations within the dataset additional structural imagery, functional imagery and findings including prior anatomical information of a patient, associated literature, and anatomical information correlated from other patients with a corresponding medical condition;

computer executable program code, responsive to a user identifying a particular formation in the analyzed view of the dataset generated by machine learning and analysis and representative of a portion of an object characterized by the dataset, for designating the particular formation using a computer recognizable gesture to identify a gestured location in the analyzed view of the dataset associated with the particular formation;

computer executable program code, responsive to identifying the gestured location, for displaying the particular formation to the user, and revealing a composition for the particular formation including additional structural imagery, functional imagery and findings resulting from the machine learning and analysis of the plurality of formations of the dataset, wherein when the machine learning and analysis are prior to completion, the revealing further comprising:

revealing the composition for the particular formation including the additional structural imagery, functional imagery and findings up to a current point of processing; and providing additional time for completion of the machine learning and analysis in response to an indication from the user; and computer executable program code, responsive to revealing the composition for the particular formation including the additional structural imagery, functional imagery and findings resulting from the machine learning and analysis for the plurality of formations, for prompting the user to select performance of one of accept selection, reject selection and modify selection with regard to the composition revealed.

10. The computer program product of claim 9, wherein the dataset is representative of information specific to data selected from a group consisting of Medical EKG/ECG data, Medical sleep study data, and Medical pathology data.

11. The computer program product of claim 9, wherein the computer recognizable gesture is an action including a single "mouse click" to identify the gestured location in the analyzed view, and wherein the dataset includes a medical image that conforms to a DICOM format.

12. The computer program product of claim 9, wherein the computer executable program code to perform accept selection further comprises:

computer executable program code for combining the particular formation, including the additional structural imagery, functional imagery and findings resulting from the machine learning and analysis associated with the particular formation displayed, with a diagnosis; and computer executable program code for generating a report including the diagnosis.

13. The computer program product of claim 9, wherein the computer executable program code to perform reject selection further comprises:

computer executable program code for prompting the user for a selection of another gestured location in a view of the particular formation, including the additional structural imagery, functional imagery and findings resulting from the machine learning and analysis associated with the particular formation displayed.

14. The computer program product of claim 9, wherein the computer executable program code to perform modify selection further comprises:
computer executable program code for presenting the particular formation corresponding to the gestured location after a modification, including the additional structural imagery, functional imagery and findings resulting from the machine learning and analysis associated with the particular formation displayed.

15. A computer program product for non-leading computer aided detection of features of interest in medical imagery, the computer program product comprising:
one or more computer readable storage media collectively containing computer executable program code stored thereon for execution by a computer, the computer executable program code comprising:
computer executable program code for receiving one or more digital images;
computer executable program code for receiving one or more of patient data, other patient data, pathological data and anatomical data, wherein the pathological data and the anatomical data are derived from one of an internal source and an external source to form a dataset including the one or more digital images received;
computer executable program code for performing an analysis of the dataset using machine learning and storing results of the machine learning and analysis after predetermined checkpoints each corresponding to performing a predetermined amount of the analysis,
wherein the analyzed data includes analysis for a plurality of formations within the dataset, and wherein the analysis using machine learning produces for the plurality of formations within the dataset additional structural imagery, functional imagery and findings including prior anatomical information of a patient, associated literature, and anatomical information correlated from other patients with a corresponding medical condition;
computer executable program code for prompting a user for a selection of a particular formation in a view of the analyzed data and revealing a composition for the particular formation including additional structural imagery, functional imagery and findings resulting from the machine learning and analysis of the plurality of formation, wherein the selection serves as a gestured location associated with the particular formation;
computer executable program code for presenting the composition corresponding to the gestured location of the user associated with the particular formation, including the additional structural imagery, functional imagery and findings resulting from the machine learning and analysis of the plurality of formations, wherein when the machine learning and analysis are prior to completion, the presenting further comprising:
revealing the composition for the particular formation including the additional structural imagery, functional imagery and findings up to a current point of processing; and
providing additional time for completion of the machine learning and analysis in response to an indication from the user;
computer executable program code for prompting the user for a selected action from a set of actions consisting of accept selection, reject selection and modify selection;
computer executable program code, responsive to the selected action being the reject selection, for prompting the user for a selection of a new gestured location in a view of the composition for the particular formation including the additional structural imagery, functional imagery and findings resulting from the machine learning and analysis of the plurality of formations;
computer executable program code, responsive to the selected action being the modify selection, for presenting the composition corresponding to the gestured location to the user associated with the particular formation after a modification, including the additional structural imagery, functional imagery and findings resulting from the machine learning and analysis of the plurality of formations;
computer executable program code, responsive to the selected action being the accept selection, for combining the composition for the particular formation, including the additional structural imagery, functional imagery and findings resulting from the machine learning and analysis of the plurality of formations, with a diagnosis; and
computer executable program code for generating a report.

16. The computer program product of claim 15, further comprising:
computer executable program code for revealing what has been identified up to a current point in processing, and indicating that a predetermined algorithm is not finished when computer executable program code for the predetermined algorithm has not finished performing the analysis;
computer executable program code for providing an indication of a current status of completion of the analysis at the current point in processing;
computer executable program code for providing an estimated time of completion of the analysis from the current point in processing; and
computer executable program code for prompting the user when finished.

17. An apparatus for non-leading computer aided detection of features of interest in a dataset, the apparatus comprising:
a communications fabric;
a memory connected to the communications fabric, wherein the memory contains computer executable program code;
a communications unit connected to the communications fabric;
an input/output unit connected to the communications fabric;
a display connected to the communications fabric; and
a processor unit connected to the communications fabric, wherein the processor unit executes the computer executable program code to direct the apparatus to:
generate an analyzed view of the dataset by analyzing the dataset using machine learning and analysis of the dataset and associated data derived from one of an internal source and an external source and store results of the machine learning and analysis after predetermined checkpoints each corresponding to performing a predetermined amount of the analyzing, wherein the analyzed view includes analysis for a plurality of formations within the dataset, and wherein the analyzing using machine learning and analysis produces for the plurality of formations within the dataset additional structural imagery, functional imagery and findings including prior anatomical information of a patient, associated literature, and anatomical information correlated from other patients with a corresponding medical condition;

designate a particular formation using a computer recognizable gesture to identify a gestured location in the analyzed view of the dataset associated with the particular formation, wherein the particular formation of the analyzed view of the dataset is representative of a portion of an object characterized by the dataset;

display, by the processor unit in response to identifying the gestured location, the particular formation to a user, and reveal a composition for the particular formation including additional structural imagery, functional imagery and findings resulting from the machine learning and analysis of the plurality of formations, wherein when the machine learning and analysis are prior to completion, the revealing further comprising:

revealing the composition for the particular formation including the additional structural imagery, functional imagery and findings up to a current point of processing; and providing additional time for completion of the machine learning and analysis in response to an indication from the user; and prompt the user to select performance of one of accept selection, reject selection and modify selection with regard to the composition revealed in response to revealing the composition to the user, wherein the composition includes the additional structural imagery, functional imagery and findings resulting from the machine learning and analysis associated with the particular formation displayed.

18. The apparatus of claim 17, wherein the dataset is representative of information specific to data selected from a group consisting of Medical EKG/ECG data, Medical sleep study data, and Medical pathology data.

19. The apparatus of claim 17, wherein the processor unit further executes the computer executable program code to direct the apparatus to:

reveal what has been identified up to a current point in processing, and indicate that a predetermined algorithm is not finished when the predetermined algorithm has not finished performing the analysis;

provide an indication of a current status of completion of the analysis at the current point in processing;

provide an estimated time of completion of the analysis from the current point in processing; and prompt the user when finished.

20. The apparatus of claim 17, wherein the computer recognizable gesture is an action including a single "mouse click" to identify the gestured location in the analyzed view, and wherein the dataset includes a medical image that conforms to a DICOM format.

21. The apparatus of claim 17, wherein the processor unit executes the computer executable program code to direct the apparatus to perform accept selection, and to further direct the apparatus to:

combine the particular formation, including the additional structural imagery, functional imagery and findings resulting from the machine learning and analysis associated with the particular formation displayed, with a diagnosis; and generate a report including the diagnosis.

22. The apparatus of claim 17, wherein the processor unit executes the computer executable program code to direct the apparatus to perform reject selection, and to further direct the apparatus to:

prompt the user for selection of another gestured location in a view of the particular formation, including the additional structural imagery, functional imagery and findings resulting from the machine learning and analysis associated with the particular formation displayed.

23. The apparatus of claim 17, wherein the processor unit executes the computer executable program code to direct the apparatus to perform modify selection, and to further direct the apparatus to:

present the particular formation corresponding to the gestured location after a modification, including the additional structural imagery, functional imagery and findings resulting from the machine learning and analysis associated with the particular formation displayed.

* * * * *